United States Patent [19]
Solon

[11] Patent Number: 4,991,337
[45] Date of Patent: Feb. 12, 1991

[54] INEXPENSIVE DISPOSABLE IDENTIFICATION BRACELET

[76] Inventor: Laurie R. Solon, 6 Squire La., St. Charles, Kane County, Ill. 60174

[21] Appl. No.: 240,720

[22] Filed: Sep. 6, 1988

Related U.S. Application Data

[63] Continuation-in-part of Ser. No. 225,379, Jul. 28, 1988.

[51] Int. Cl.[5] .................... A61B 5/00
[52] U.S. Cl. .................... 40/633; 40/665
[58] Field of Search .................... 40/633, 665, 630; 24/16 PB, 16 R

[56] References Cited

U.S. PATENT DOCUMENTS

| | | | |
|---|---|---|---|
| 2,561,894 | 7/1951 | Wallich | 40/633 |
| 3,153,869 | 10/1964 | Twentier | 40/633 |
| 4,088,136 | 5/1978 | Hasslinger et al. | 24/16 R |
| 4,257,596 | 3/1981 | Capella | 24/16 PB |
| 4,318,234 | 3/1982 | Charles et al. | 40/665 |
| 4,612,718 | 9/1986 | Golub et al. | 40/633 |
| 4,682,431 | 7/1987 | Kowalchuk | 40/633 |
| 4,712,766 | 12/1987 | Ehrenhalt | 24/16 PB |

*Primary Examiner*—Gene Mancene
*Assistant Examiner*—Michael Lynch
*Attorney, Agent, or Firm*—Wood, Phillips, Mason, Recktenwald & Vansanten

[57] ABSTRACT

An inexpensive, readily disposable identification bracelet is formed by a strip 10 of thin, but tough, flexible material and has identification indicia 22, 24, 26 on its top side 16 defining locations 28, 30, 32 for receipt of variable information that may be placed thereon by pen, pencil, typewriter or the like. Opposite ends, 12, 14, have, on opposite sides 16, 18 of the strip 10, respective bodies 40, 46 of pressure sensitive adhesive whereby the ends 12 and 14 may be overlapped and secured together.

2 Claims, 1 Drawing Sheet

INEXPENSIVE DISPOSABLE IDENTIFICATION BRACELET

CROSS REFERENCE

This application is a continuation-in-part of my copending application Ser. No. 225,379, filed July 28, 1988, and entitled, "Inexpensive Disposable Identification Bracelet".

FIELD OF THE INVENTION

This invention relates to identification bracelets, and more specifically, to an identification bracelet that is inexpensive and therefore readily disposable after a very short period of use.

BACKGROUND OF THE INVENTION

Increasingly, children of relatively tender years are called upon to travel. In some instances, the travel may be with groups such as school classes, church groups, scouting organizations or the like that are supervised by adults. Generally, the ratio of supervising adults to the number of children in such a group is sufficiently small that one ore more children within the group may momentarily escape notice and, for any of a variety of reasons, become lost.

In other instances, such children may travel individually from one section of the country to another to visit relatives, separated parents or the like. Because of their age, they may readily become disoriented during the course of the trip due to the strangeness of surroundings, the large number of people about them, etc.

Thus, it can be readily appreciated that in both of the above instances, as well as in others that will readily occur to those skilled in the art, there is a need whereby such children can be provided with some sort of identification that may be used by travel personnel, municipal or state authorities, etc. to identify the child and/or determine the next step in the child's trip.

Certain of the airlines have attempted to meet this problem through the use of pressure sensitive labels much like those used at large social gatherings where not all of the attendees are acquainted with each other. While such labels solve the problem to some degree, they are readily pealed from clothing of the wearer and young children in particular are apt to "play" or otherwise toy with such labels resulting in their removal and/or obliteration.

The present invention is directed to overcoming one or more of the above problems.

SUMMARY OF THE INVENTION

It is the principal object of the invention to provide a new and improved, inexpensive, readily disposable means of identification particularly suited for use by young children when traveling by themselves or in groups. More specifically, it is an object of the invention to provide such a means of identification in the form of an identification bracelet.

An exemplary embodiment of the invention achieves the foregoing objects in a structure including an elongated strip of thin, but tough, flexible material having first and second opposed ends and first and second opposed sides. The first side has a surface that can receive and retain variable information written at a desired location thereon with a pencil, typewriter, pen or the like. A first body of pressure sensitive adhesive is disposed on the first side adjacent the first end and a second body of pressure sensitive adhesive is located on the second side adjacent the second end. As a consequence of this construction, variable information may be inscribed at the desired locations on the first side, the strip disposed about the limb of a wearer with the first side adjacent or remote from the wearer and the ends brought into superimposed relation with a part of the first side near the one end while being subjacent a part of the bottom side near the other end, and pressure applied to the strip oppositely of each body of adhesive to secure each end of the strip to the adjacent superimposed part of the strip.

As a result of the foregoing, the bracelet may be worn either with the variable information exposed when the first side is remote from the wearer or with the variable information hidden when the first side is abutting the wearer. In either event, the variable information identifying the child and/or the child's itinerary is available for ready viewing by travel personnel, municipal authorities or the like. At the same time, both ends of the strip are firmly secured to the strip so there are no loose ends which may be readily snagged to cause the bracelet to disassociated from the wearer. Furthermore, even if one of the bodies of pressure sensitive adhesive should become disassociated from the superimposed part of the strip to which it is intended to adhere, there remains a second body of adhesive securing the ends of the strip together as a backup.

In a highly preferred embodiment, the first side of the strip is provided with identification indicia printed thereon. The identification indicia in turn defines locations for receipt of the variable information.

In a highly preferred embodiment, the pressure sensitive adhesive bodies are of the type that may be covered with separate release liners. Thus, the adhesive is protected during the inscription operation but may be exposed simply by removing the release liners.

Other objects and advantages will become apparent from the following specification taken in connection with the accompanying drawings.

DESCRIPTION OF THE PREFERRED EMBODIMENT

Figure 1:
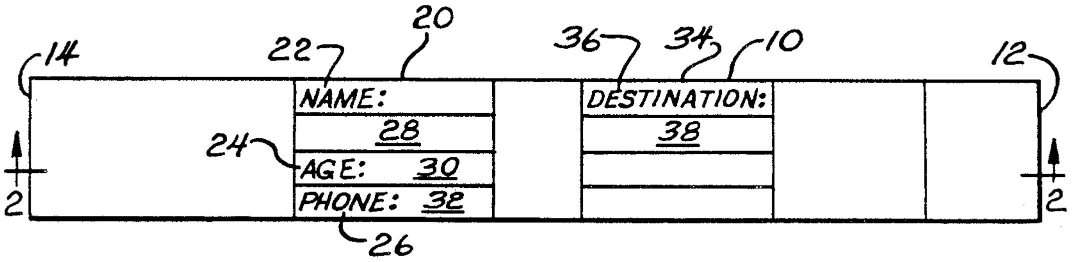
FIG. 1 is a plan view of an identification bracelet made according to the invention.

An exemplary embodiment of an inexpensive, readily disposable identification bracelet made according to the invention is illustrated in the drawings and with reference thereto is seen to include an elongated strip 10 of thin, but tough, flexible material. Various sorts of plastic, papers or even certain inexpensive fabric, or combinations thereof might be utilized to form the strip. The strip 10 includes opposed ends 12 and 14 as well as a top or first side 16 and a bottom or second side 18.

The top side 16 is characterized by the ability to receive variable information by inscription thereon through the use of a pen, pencil, typewriter or the like.

Depending upon the material of which the strip 10 is formed, this may or may not require special treatment of the top side 16. In a highly preferred embodiment, the strip 10 is formed of a paper known in the printing trade as "FPG 250 Kimdura". This material is sufficiently tough that it cannot be readily torn by children and yet may be inscribed upon with ball point pen without requiring any modification or treatment of the surface 16.

In addition, such material will receive printing of personal identification information. As seen in FIG. 1, at a location 20 intermediate the ends 12 and 14, name indicia 22 is printed along with age indicia 24 and phone indicia 26. The printing also provides a number of blanks 28, 30 and 32 for receipt of the corresponding variable information.

Desirably, the top side 16 may include additional printing in an area 34. Such printing may include itinerary indicia 36 and associated locations 38 for receipt of variable information relating to the itinerary. Like the area 20, the area 34 is intermediate the ends 12 and 14.

Figure 2:
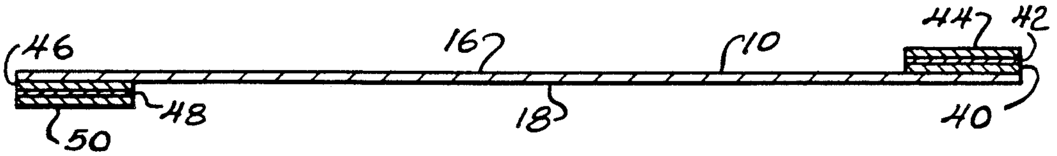
FIG. 2 is a sectional view taken approximately along the line 2—2 of FIG. 1 with certain parts exaggerated in size for clarity.

As can be seen in FIGS. 1 and 2, the end 12 of the strip 10, on the top side 16 thereof, is provided with a body 40 of pressure sensitive adhesive. The pressure sensitive adhesive in turn is contacted by the waxy surface layer 42 of a conventional release liner 44.

A second body of pressure sensitive adhesive 46 is disposed on the bottom side 18 of the strip 10 adjacent the end 14. Its exposed side is similarly contacted by the waxy surface 48 on a conventional release liner 50.

To use the bracelet of the invention, variable information is entered in the area 20 and the area 34 if applicable. The release liners 44 and 50 are then stripped from the respective bodies 40 and 46 of pressure sensitive adhesive to expose the same. The strip 10 may then be coiled about the limb of the child to whom the bracelet is to be attached. The outline of such a limb is shown somewhat schematically in dotted lines at 52 in FIG. 3 and typically will be a wrist or the like although narrowed parts of other appendages might be used if desired. Depending on the desires of the person applying the bracelet, the top side 16 may be either remote from or adjacent to the limb of the wearer.

Figure 3:
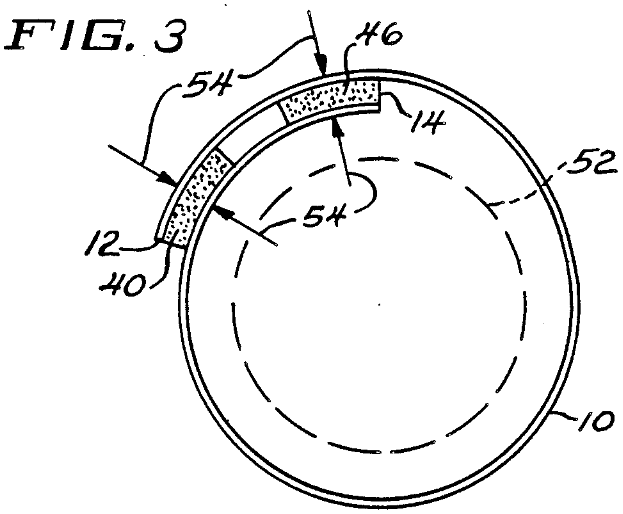
FIG. 3 is a side elevation of the identification bracelet in one way it would appear while on the limb of a wearer.

The end 12 is caused to overlap the end 14 such that the bodies 40 and 46 of pressure sensitive adhesive are in somewhat facing relation although they may be displaced to one side of each other as illustrated in FIG. 3. Pressure is then applied in the direction of the arrows 54 shown in FIG. 3 to bring the superimposed part of the strip 10 into contact with the adjacent exposed part of the corresponding body 40 and 46 of pressure sensitive adhesive thereby securing the strip 10 in the loop-like form illustrated in FIG. 3. It will be readily recognized that either one of the bodies 40 and 46 of pressure sensitive adhesive could loosen and there would still be retention of the bracelet.

When the top side 16 is remote from the wearer, the variable information received in the blanks 28, 30, 32, 38 will be readily visible for inspection by travel personnel, etc. In some instances, particularly with small children who might respond to a stranger who might see the child's name inscribed in one of the blanks and could thus call the child's name, it may be desirable and even preferable that the variable information be hidden, though nonetheless relatively readily available. In such a case one need only apply the bracelet with the top side 16 and the variable information thereon facing the wearer, that is, with the top side 16 abutting the limb of the wearer. Access to the variable information may thus be readily had by breaking the adhesion of the bodies 40 and 46 and removing the bracelet which later may be reapplied as desired.

It will also be recognized that because the strip 10 is formed of an inexpensive material as are the locking means which are made of pressure sensitive adhesive, a very inexpensive identification bracelet results. Thus, it is ideally suited for use with children on field trips, or children traveling alone over periods of relatively short duration. After those trips have been completed, the bracelet may be easily removed and discarded. Because the bracelet is made of strips of thin paper or plastic-like material, several of the bracelets may be readily stacked and packaged, allowing parents, travel agencies, commercial carriers or the like to maintain supplies on hand for immediate use when required.

I claim:

1. An inexpensive disposable identification bracelet comprising:

an elongated strip of thin but tough flexible material having first and second opposed ends and top and bottom opposed sides;

said top side having a surface that will receive and retain variable information written thereon with a pen, pencil, typewriter or the like;

identification indicia printed on said top side and defining locations for receipt of said variable information;

a first body of pressure sensitive adhesive on said top side adjacent said first end;

a second body of pressure sensitive adhesive on said bottom side adjacent said second end; and removable release liners covering said bodies of adhesive;

whereby variable information may be inscribed at said locations, the release liners removed, the strip disposed about a limb of a wearer with said top side facing or remote from the wearer, the ends brought into superimposed relation with said adhesive bodies facing each other and pressure applied to the strip oppositely of each body of adhesive to secure each end of the strip to the adjacent superimposed part of the strip.

2. An identification bracelet comprising:

an elongated strip of thin but tough flexible material having first and second opposed ends and top and bottom opposed sides;

said top side having a surface that will receive and retain variable information written at a desired location thereon with a writing instrument or the like;

a first body of pressure sensitive adhesive on said top side adjacent said first end; and a second body of pressure sensitive adhesive on said bottom side adjacent said second end;

whereby variable information may be inscribed at said locations, the strip disposed about a limb of a wearer with said top side facing or remote from the wearer, the ends brought into superimposed relation with a part of said top side near said first end being subjacent a part of said bottom side near said second end and with said adhesive bodies facing each other and pressure applied to the strip oppositely of each body of adhesive to secure each end of the strip to the adjacent superimposed part of the strip.

* * * * *